United States Patent [19]

Roberts

[11] 4,377,382
[45] Mar. 22, 1983

[54] DENTURE SUPPORT FRAME

[76] Inventor: Ralph A. Roberts, 920 Rio Dell Ave., Rio Dell, Calif. 95562

[21] Appl. No.: 220,018

[22] Filed: Dec. 24, 1980

Related U.S. Application Data

[63] Continuation-in-part of Ser. No. 69,592, Aug. 24, 1979.

[51] Int. Cl.³ .......................................... A61C 13/00
[52] U.S. Cl. .................................................... 433/176
[58] Field of Search ............................... 433/173, 176

[56] References Cited

U.S. PATENT DOCUMENTS

| | | | |
|---|---|---|---|
| 3,908,269 | 9/1975 | Christenot | 433/176 |
| 4,202,099 | 5/1980 | Roberts | 433/176 |

*Primary Examiner*—Robert Peshock
*Attorney, Agent, or Firm*—Eugene M. Eckelman

[57] ABSTRACT

A rigid bar arranged to removably support an artificial denture is curved substantially to the longitudinal contour of the lower jaw bone. This bar has a front support arranged to be implanted in a front recess in the jaw bone and also includes a rear ramus implant portion on each side arranged to be implanted in the ramus portions of the jaw bone. Each of the ramus implant portions comprises a plate-like extension of the rigid bar having laterally facing surfaces. This rearward plate-like extension has an elongated length so as to project above or below the plane of the bar or in a preferred construction, such extension projects both above and below such bar to provide an extended implant attachment to the jaw bone structure. The plate-like extension angles forwardly from top to bottom so that it can be embedded efficiently in the rearward portion of the jaw bone. Such rearward plate-like extensions also include laterally extending tabs arranged to seat on the jaw bone for further adding to support for the ramus implant portions.

6 Claims, 9 Drawing Figures

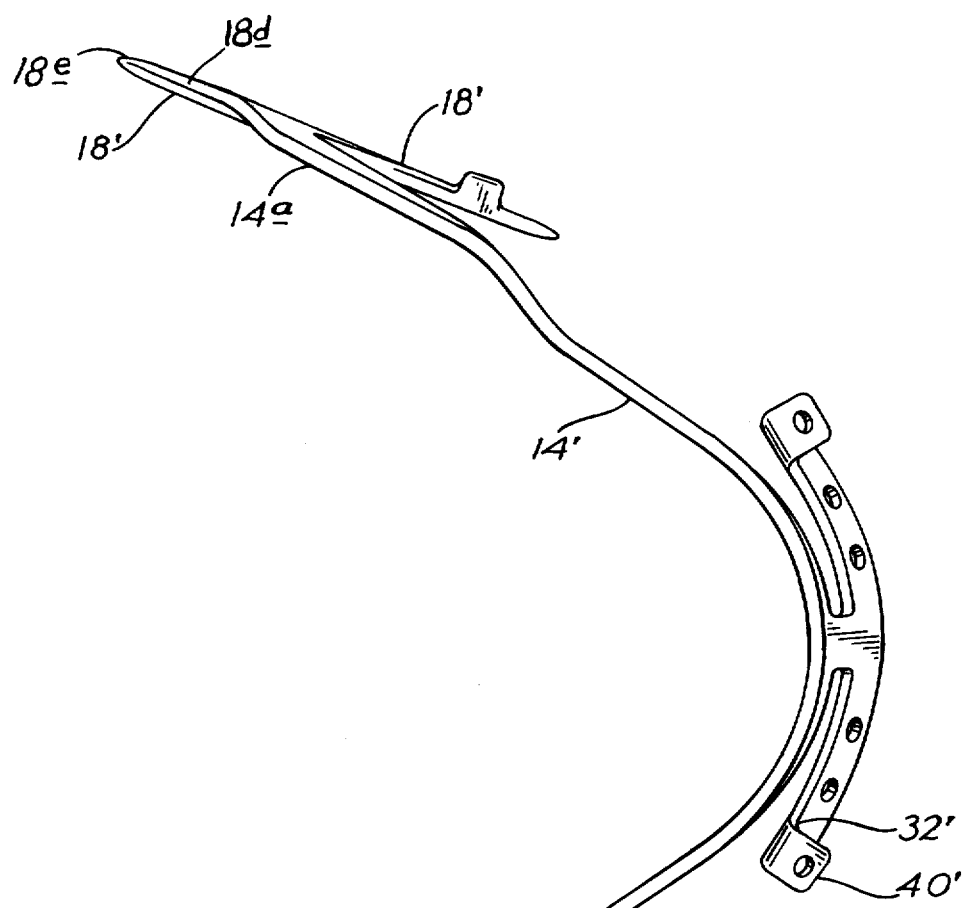
FIG. 7
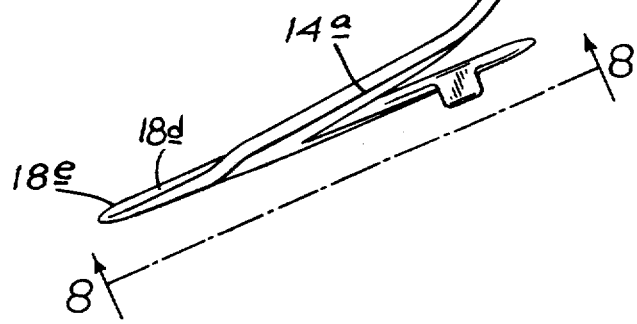
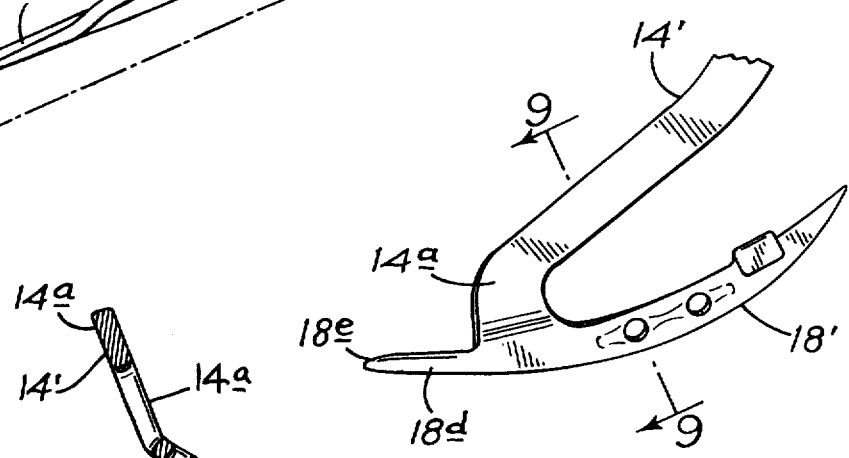
FIG. 9    FIG. 8

DENTURE SUPPORT FRAME

REFERENCE TO PRIOR APPLICATIONS

This is a continuation-in-part of application Ser. No. 69,592, filed Aug. 24, 1979 for Denture Support Frame.

BACKGROUND OF THE INVENTION

This invention relates to new and useful improvements in denture support frames and is particularly concerned with improvements in such frames for use with lower dentures.

Denture support frames for lower dentures have heretofore been employed which consist of a rigid bar properly sized and contoured substantially to the longitudinal shape of the lower jaw bone. One such prior structure, for example, is shown in U.S. Pat. No. 3,641,671, wherein the rigid bar has rear portions which are implanted in recesses cut in the ramus portions of the jaw. A forward portion of the bar has an integral downward extension arranged to be implanted at the forward portion of the jaw bone. Although prior implant portions provide a substantially sturdy connection for the denture support bar, the rear implant portions, in some of the more difficult cases allow undesirable settling or loosening of the support bar as a result of a lack of connected and supported areas in the jaw bone.

SUMMARY OF THE INVENTION

According to the present invention and forming a primary objective thereof, a denture support frame for lower dentures is provided having an improved implant structure for increasing the connected and supported area for a denture support bar in the jaw bone, thus reducing the possibility of settling and loosening of the support means.

The objectives of the invention are achieved by structure including a rigid bar curved substantially to the longitudinal contour of the lower jaw bone, and in addition to having front support means for implant in the front portion of the jaw bone, such bar includes rear plate-like extensions arranged to be implanted in the rear portion of the jaw bone. Importantly, these rearwardly or forwardly plate-like extensions project, or relative to the rear of the bar to provide an extended implant attachment to jaw bone structure, and the ends thereof are shaped for maximum fit and hold in the jaw bone. In order to provide the most efficient implant connection to the rear portion of the jaw, said plate-like extensions angle downwardly toward the front, and to further increase the support area for the implant, these plate-like extensions can include laterally extending tab means arranged to seat on the jaw bone.

The invention will be better understood and additional objects and advantages will become apparent from the following description taken in connection with the accompanying drawings.

BRIEF DESCRIPTION OF THE DRAWINGS

FIG. 7 is a plan view of a modified denture support frame embodying features of the invention;

FIG. 8 is a fragmentary side elevational view taken on the line 8—8 of FIG. 7; and FIG. 9 is a sectional view taken on the line 9—9 of FIG. 8.

DETAILED DESCRIPTION OF A PREFERRED EMBODIMENT

Figure 1:
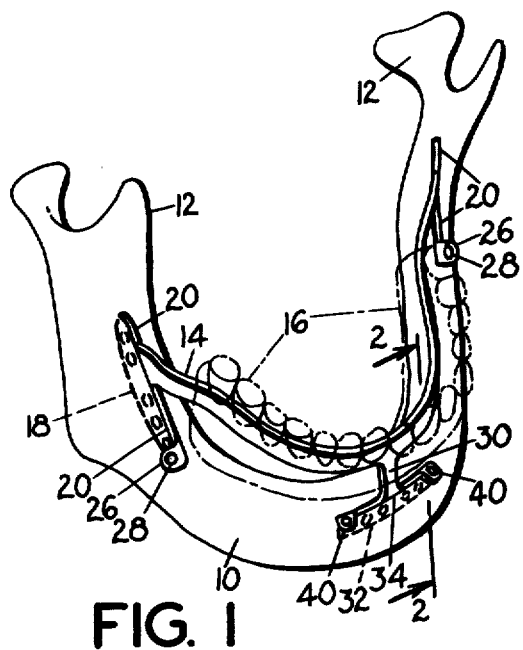
FIG. 1 is a perspective view of a jaw bone having a first form of denture support of the present invention mounted therein, a denture tooth base member being shown in broken lines.

With particular reference to the drawings, and first to FIGS. 1-6 showing a first embodiment, the numeral 10, FIG. 1, designates a jaw bone and the numeral 12 designates opposite ramus portions thereof. The denture support frame of the instant invention comprises a rigid bar 14 which is curved substantially to conform to the longitudinal shape of the jaw bone, such exact shaping and sizing being accomplished by the dentist with suitable tools prior to attachment of the bar in the mouth. The numeral 16 represents a denture member, also seen in FIG. 2, arranged to be supported on the bar 14.

Figure 6:
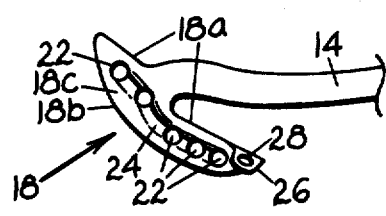
FIG. 6 is a fragmentary side elevational view taken on the line 6—6 of FIG. 3.

The rigid bar 14 has rear blade or plate-like extensions 18, best seen in FIGS. 1 and 6, arranged to be inserted in suitably contoured and dimensioned recesses 20 cut by the dentist in the rearward portion of the jaw bone. In a preferred arrangement to provide good implanting in the ramus portion as well as in a portion of the jaw forward of the ramus portion, the extensions 18 angle downwardly toward the front and extend above and below the plane of the bar 14, or in other words portions thereof extend rearwardly and forwardly of the connection with the bar. It is to be understood, however, that sufficient implant area could be obtained by the extension 18 projecting either rearwardly or forwardly of the rear of the bar 14 since sufficient bone structure may in some cases be provided in the ramus or forward portions of the jaw bone to provide the necessary implant area.

In receiving the extension 18 of the shape shown in FIG. 6, the recess 20 in the jaw bone will be cut to extend upwardly in the ramus portion 12 and also partly along the horizontal portion in front of the ramus portion. The top or forwardly facing edge 18a of the extension 18 is substantially straight, and the bottom or rearwardly facing edge 18b is somewhat convex, such contour being found to provide an efficient implant connection in most cases. These edge portions provide good implant connection in the jaw bone and also fit in a recess which is easily cut.

As shown, the plate-like extension 18 has laterally facing surfaces 18c which provide an efficient implant connection with the jaw bone, and in addition such extension has laterally extending apertures 22 to receive bone growth. Further yet, the side surfaces 18c have longitudinal, concaved portions 24 along substantially the line of the apertures 22, such concaved portions also receiving bone growth to provide maximum implant connection.

In some cases it may be desired to provide extra support for the implant portions 18, and for this purpose a forward laterally extending tab 26 is provided as an integral part of the extensions. The tabs 26 extend outwardly and are arranged to seat on the top surface of the jaw bone. They are slightly rounded to conform to the upper surface contour of the jaw bone and may or may not be recessed into the jaw bone. They have an aperture 28 therethrough which can receive bone growth if recessing in the jaw bone is provided.

Figure 2:
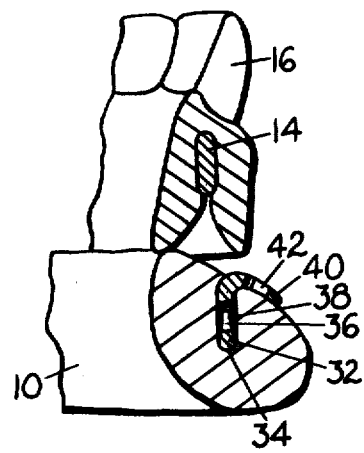
FIG. 2 is an enlarged sectional view taken on the line 2—2 of FIG. 1 and showing the denture tooth base member in full lines.
Figure 4:
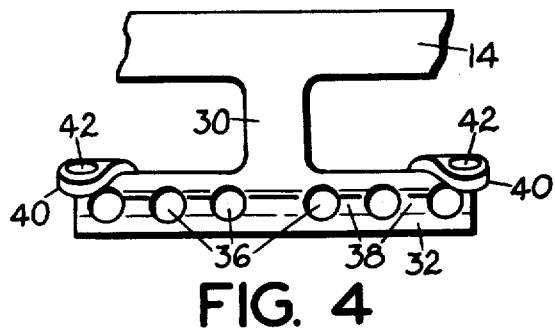
FIG. 4 is an enlarged fragmentary front elevational view taken on the line 4—4 of FIG. 3.
Figure 3:
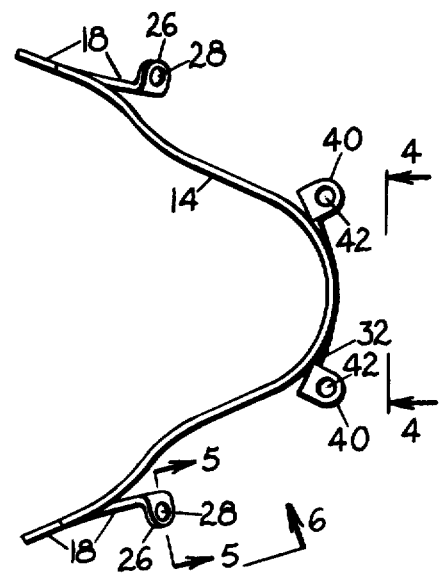
FIG. 3 is a plan view of the denture support frame of FIG. 1.
Figure 5:
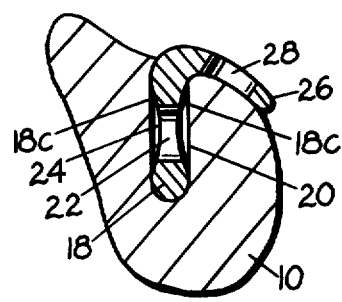
FIG. 5 is an enlarged sectional view taken on the line 5—5 of FIG. 3 and showing an implant portion of the frame of FIG. 1 installed in the jaw bone.

Bar 14 is provided with a front depending extension 30 having an integral cross blade portion 32 which is substantially parallel with the bar 14 and which is arranged to extend into a recess 34, best seen in FIG. 2, cut in a front portion of the jaw bone by the dentist. The blade portion 32 has a plurality of apertures 36 to receive bone growth, and in addition, both the forward and rearward surfaces of this cross blade portion have longitudinal, concaved portions 38 along the line of the apertures. This concaved portion also receives bone growth. The blade portion 32 steadies the front portion of the bar 14 and also provides good support against downward biting forces of the front teeth. Integral forwardly facing tabs 40 may be provided at the ends of the blade portion 32 for seating on a jaw bone surface to increase the bearing support for the bar 14. These tabs may or may not be recessed into the jaw bone and have apertures 42 to receive bone growth in the event that recessing in the jaw bone is provided.

In the embodiment shown in FIGS. 7-9, a one-piece support bar 14' is provided as in the FIG. 1 embodiment, and this bar similarly terminates at its rearward free ends in blade or plate-like extensions 18'. Bar 14' has a front implant portion of the same structure as that shown in FIG. 1, comprising a depending cross blade portion 32' and forwardly facing tabs 40'.

The embodiment of FIGS. 7-9 differs from the first embodiment in the structure of the rear plate-like implant extensions 18'. While such extensions have portions thereof extending both rearwardly and forwardly of the connection with the bar 14', or since the extension is angled it can be considered to extend above and below the bar, the rearwardly extending portion 18d is thinned to a spike-like shape 18d. Portion 18d is of substantially uniform width and thickness and has a pointed or sharpened end 18e.

The spike-like portion 18d has a sharpened end 18e which allows the portion 18d to be forced into the jaw bone just below the corticle bone. The corticle bone comprises extremely hard bone but the bone just below it is softer. This allows the portion 18d to be driven into the softer bone without cutting a bore or recess. Such process not only speeds up the installation of the implant but also provides an instantaneous and firm hold in the jaw bone. The remainder of the extension 18', namely, the lower portion, is laid in a recess cut in the bone as in the FIG. 1 embodiment.

In order to accomplish the desired implanting of the blade extensions 18' and with reference to FIG. 8, the bar 14' has an angular portion 14a at its juncture with the extension 18', such angular portion meeting the extension at approximately a right angle. This particular jointing arrangement allows for the formation of the rear spike end 18d and its forced insertion into the jaw bone. With reference to FIGS. 7 and 9, the rear portions 14a of the bar 14' are twisted or angled inwardly so as to lead away from and provide clearance with the sides of the mouth.

It is to be understood that the forms of my invention herein shown and described are to be taken as preferred examples of the same and that various changes in the shape, size and arrangement of parts may be resorted to without departing from the spirit of my invention, or the scope of the subjoined claims.

Having thus described my invention, I claim:

1. A denture support frame arranged to be attached to the horizontal portion of the lower jaw bone as well as to the upwardly directed rear ramus portion thereof, said support frame comprising
    (a) a one-piece rigid bar arranged to support an artificial denture thereon,
    (b) said bar having front and rear portions and being curved substantially to the longitudinal contour of the lower jaw bone,
    (c) said bar having a rear ramus implant portion on each side arranged to be implanted in a recess cut in the jaw bone,
    (d) front support means on said bar arranged for engagement with the jaw bone,
    (e) each of said ramus implant portions comprising a rear plate-like extension of said bar having laterally facing surfaces and upper and lower ends,
    (f) said rear plate-like extension projecting rearwardly and forwardly of the rearward end of said bar to provide an extended implant attachment to jaw bone structure,
    (g) and laterally extending tab means on said rearwardly directed plate-like extensions arranged to seat on the jaw bone for further adding to support area for the ramus implant portions.

2. The denture support frame of claim 1 wherein said rearwardly directed plate-like extensions extend both above and below the plane of said bar and said tab means is disposed at the lower end thereof.

3. A denture support frame arranged to be attached to the horizontal portion of the lower jaw bone as well as to the upwardly directed rear ramus portion thereof, said support frame comprising
    (a) a one-piece rigid bar arranged removably to support an artificial denture thereon,
    (b) said bar having front and rear portions and being curved substantially to the longitudinal contour of the lower jaw bone,
    (c) said bar having a rear ramus implant portion on each side arranged to be implanted in the jaw bone,
    (d) and front support means on said bar arranged for engagement with the jaw bone,
    (e) each of said ramus implant portions comprising a blade extending forwardly from the rear of said bar arranged to be implanted in recesses suitably cut in the jaw bone,
    (f) said ramus implant portions also including a spike-like structure of substantially uniform width and thickness projecting rearwardly from the rear of said bar and terminating in a pointed end, said spike-like structures being arranged to be forcibly driven rearwardly into the ramus portions of the jaw bone,
    (h) said blades and spike-like structures being angled downwardly relative to said bar to allow said blades to be set in recesses cut in the ramus portions of the jaw bone and portions of the jaw bone forwardly of the ramus portions and to allow said spike-like structures to be driven upwardly into the ramus portions of the jaw bone.

4. The denture support frame of claim 3 wherein rearward portions of said bar adjacent said blades are angled inwardly from the bottom thereof to the top to provide clearance with the sides of the mouth.

5. The denture support frame of claim 3 wherein said bar includes downwardly angled rearward end portions connecting said bar and said blades, said rearward end portions joining with said blades at approximately a right angle.

6. The denture support frame of claim 3 including laterally extending tab means on a forward portion of said blades arranged in the implanted position of said blades to seat on the jaw bone for further adding to support area for the ramus implant portions.

* * * * *